US011894135B2

(12) United States Patent
Dickinson et al.

(10) Patent No.: US 11,894,135 B2
(45) Date of Patent: *Feb. 6, 2024

(54) CLOUD COMPUTING ENVIRONMENT FOR BIOLOGICAL DATA

(71) Applicant: Illumina, Inc., San Diego, CA (US)

(72) Inventors: Alexander G Dickinson, Laguna Beach, CA (US); Francisco Jose Garcia, San Diego, CA (US); Robert C. Kain, San Diego, CA (US); Scott D. Kahn, Rancho Santa Fe, CA (US); Andrew R. Nelson, England (GB)

(73) Assignee: Illumina, Inc., San Diego, CA (US)

(*) Notice: Subject to any disclaimer, the term of this patent is extended or adjusted under 35 U.S.C. 154(b) by 334 days.

This patent is subject to a terminal disclaimer.

(21) Appl. No.: 17/316,247

(22) Filed: May 10, 2021

(65) Prior Publication Data
US 2021/0265056 A1    Aug. 26, 2021

Related U.S. Application Data

(60) Division of application No. 16/259,434, filed on Jan. 28, 2019, now Pat. No. 11,031,132, which is a (Continued)

(51) Int. Cl.
G16H 40/67     (2018.01)
G16H 40/40     (2018.01)
(Continued)

(52) U.S. Cl.
CPC ......... G16H 40/67 (2018.01); G06F 21/6218 (2013.01); G16B 30/10 (2019.02);
(Continued)

(58) Field of Classification Search
CPC ........ G16H 40/67; G16H 40/40; G16H 40/63; G16B 30/10; G16B 50/00; G16B 50/10;
(Continued)

(56) References Cited

U.S. PATENT DOCUMENTS 6,172,218 B1   1/2001   Brenner
6,306,597 B1   10/2001  Macevicz
(Continued)

FOREIGN PATENT DOCUMENTS

WO    2005065814 A1    7/2005
WO    2006064199 A1    6/2006
(Continued)

OTHER PUBLICATIONS

Batley, Jacqueline, "Genome sequence data: management, storage, and visualization," BioTechniques, 46:333-336 (Apr. 2009).
(Continued)

*Primary Examiner* — Thanh T Le
(74) *Attorney, Agent, or Firm* — Fletcher Yoder, P.C.

(57) ABSTRACT

The present invention provides a novel approach for storing, analyzing, and/or accessing biological data in a cloud computing environment. Sequence data generated by a particular sequencing device may be uploaded to the cloud computing environment during a sequencing run, which reduces the on-site storage needs for the sequence data. Analysis of the data may also be performed in the cloud computing environment, and the instructions for such analysis may be set at the originating sequencing device. The sequence data in the cloud computing environment may be shared according to permissions. Further, the sequence data may be modified or annotated by authorized secondary users.

15 Claims, 11 Drawing Sheets

Related U.S. Application Data continuation of application No. 15/258,651, filed on Sep. 7, 2016, now Pat. No. 10,223,502, which is a continuation of application No. 13/790,596, filed on Mar. 8, 2013, now Pat. No. 9,444,880.

(60) Provisional application No. 61/622,763, filed on Apr. 11, 2012.

(51) Int. Cl.

| | | |
|---|---|---|
| *G16H 40/63* | (2018.01) | |
| *G16B 30/10* | (2019.01) | |
| *G16B 50/00* | (2019.01) | |
| *G16B 50/10* | (2019.01) | |
| *G16B 50/30* | (2019.01) | |
| *H04L 67/10* | (2022.01) | |
| *G06F 21/62* | (2013.01) | |
| *H04L 9/40* | (2022.01) | |

(52) U.S. Cl.
CPC ............ *G16B 50/00* (2019.02); *G16B 50/10* (2019.02); *G16B 50/30* (2019.02); *G16H 40/40* (2018.01); *G16H 40/63* (2018.01); *H04L 63/08* (2013.01); *H04L 63/102* (2013.01); *H04L 67/10* (2013.01)

(58) Field of Classification Search
CPC ..... G16B 50/30; G06F 21/6218; H04L 63/08; H04L 63/102; H04L 67/10
USPC .......................................................... 726/4
See application file for complete search history.

(56) References Cited

U.S. PATENT DOCUMENTS

| | | | | |
|---|---|---|---|---|
| 6,530,065 | B1* | 3/2003 | McDonald | G06F 30/367 716/136 |
| 6,865,596 | B1* | 3/2005 | Barber | H04L 12/282 709/208 |
| 6,969,488 | B2 | 11/2005 | Bridgham et al. | |
| 7,001,792 | B2 | 2/2006 | Sauer et al. | |
| 7,057,026 | B2 | 6/2006 | Barnes et al. | |
| 7,870,044 | B2 | 1/2011 | Robertson | |
| 8,241,573 | B2 | 8/2012 | Banerjee et al. | |
| 8,244,479 | B2 | 8/2012 | Kain et al. | |
| 8,555,273 | B1* | 10/2013 | Chia | G06F 8/654 717/172 |
| 9,444,880 | B2 | 9/2016 | Dickinson et al. | |
| 9,971,871 | B2* | 5/2018 | Arrizza | G16H 70/40 |
| 2005/0100900 | A1 | 5/2005 | Kawashima et al. | |
| 2006/0188901 | A1 | 8/2006 | Barnes et al. | |
| 2006/0203783 | A1* | 9/2006 | Gahler | B60T 8/885 370/338 |
| 2006/0240439 | A1 | 10/2006 | Smith et al. | |
| 2006/0281109 | A1 | 12/2006 | Barr et al. | |
| 2007/0166705 | A1 | 7/2007 | Milton et al. | |
| 2009/0026082 | A1 | 1/2009 | Rothberg et al. | |
| 2009/0127589 | A1 | 5/2009 | Rothberg et al. | |
| 2010/0056877 | A1 | 3/2010 | Fein et al. | |
| 2010/0083303 | A1 | 4/2010 | Redei et al. | |
| 2010/0088205 | A1 | 4/2010 | Robertson | |
| 2010/0137143 | A1 | 6/2010 | Rothberg et al. | |
| 2010/0282617 | A1 | 11/2010 | Rothberg et al. | |
| 2010/0299313 | A1 | 11/2010 | Orsini et al. | |
| 2010/0299763 | A1 | 11/2010 | Marcus et al. | |
| 2011/0035594 | A1 | 2/2011 | Fox | |
| 2011/0179111 | A1 | 7/2011 | Ravichandran et al. | |
| 2011/0179141 | A1 | 7/2011 | Ravichandran et al. | |
| 2011/0196908 | A1 | 8/2011 | Sukthankar et al. | |
| 2011/0220775 | A1 | 9/2011 | Triener et al. | |
| 2011/0289497 | A1* | 11/2011 | Kiaie | G06F 11/1433 709/221 |
| 2011/0301441 | A1 | 12/2011 | Bandic et al. | |
| 2012/0020537 | A1 | 1/2012 | Garcia et al. | |
| 2012/0110033 | A1 | 5/2012 | Park et al. | |
| 2012/0124666 | A1 | 5/2012 | Kim et al. | |
| 2012/0203823 | A1 | 8/2012 | Manglik et al. | |
| 2012/0237928 | A1 | 9/2012 | Rava et al. | |
| 2012/0239424 | A1* | 9/2012 | Romans | G16H 40/67 705/2 |
| 2012/0270305 | A1 | 10/2012 | Reed et al. | |
| 2012/0322439 | A1* | 12/2012 | Ding | H04W 24/00 455/425 |
| 2012/0331528 | A1 | 12/2012 | Fu et al. | |
| 2013/0096943 | A1* | 4/2013 | Carey | G16B 50/40 705/2 |
| 2013/0110775 | A1 | 5/2013 | Forsythe | |
| 2013/0116750 | A1* | 5/2013 | Schmidt | G16H 40/67 607/59 |
| 2013/0184999 | A1 | 7/2013 | Ding | |
| 2014/0012843 | A1* | 1/2014 | Soon-Shiong | G16B 30/00 707/736 |
| 2014/0032125 | A1 | 1/2014 | Hawkins | |
| 2014/0075183 | A1 | 3/2014 | Wang et al. | |
| 2018/0089029 | A1* | 3/2018 | Resch | H04L 9/3247 |

FOREIGN PATENT DOCUMENTS

| | | |
|---|---|---|
| WO | 2007010251 A2 | 1/2007 |
| WO | 2011067559 A1 | 6/2011 |

OTHER PUBLICATIONS

Coates, Guy, "Cloud Computing for Biology," Cloudscape III, Mar. 15, 2011 (http://www.sienainitiative.eu/Repository/FileScaricati/4901edb1-2976-43f2- b3a8-92f6c8ccd584.pdf).

Cockroft, et al., "A Single Molecule Nanopore Device Detects DNA Polymerase Activity With Single Nucleotide Resolution", J. Am. Chem. Soc. 130(3), 818-820 (2008).

D'Ascenzo, Mark D., "PeerGAD: a peer-review-based and community-centric web application for viewing and annotating prokaryotic genome sequences", 32(10):3124-3135, 61112.004.

Davies, Kevin, "PacBio's Eleven: Pacific Biosciences Announces Founding Technology Partners," Bio-IT World, Feb. 16, 2010 (http://www.bio- itworld.com/2010/02/16/pacbio11.html ).

Dd, "HiSeq 2000," PollTiGenomics, Jan. 12, 2010, retrieved on Dec. 5, 2013.

DNAnexus Quick Start Guide Version 1.0, Dec. 15, 2010.

DNAnexus Upload Agent User Guide Version 1.3, Mar. 16, 2011.

DNAnexus User Guide Version 1.8, Jul. 29, 2010.

Healy, "Nanopore-based single-molecule DNA analysis", Nanomed. 2(4), 459-481 (2007).

Illumina, "Single-Read Sequencing User Guide for Cluster Station and Genome Analyzer II," Jul. 2008 (http://sfgf.stanford.edu/documents/solexa_docs/User_Manuals/SingleRead_Sequencing_UserGuide_GAil_1004831_Rev_A.pdf).

Korlach et al., "Selective aluminum passivation for targeted immobilization of single DNA polymerase molecules in zero-mode waveguide nanostructures", Proc_ Natl. Acad. Sci. 105(4), 1176-1181 (2008).

Levene et al., "Zero-Mode Waveguides for Single-Molecule Analysis at High Concentrations," Science vol. 299, 682-686 (2003).

Lundquist et al., "Parallel confocal detection of single molecules in real time", Opt Lett. 33(9), 1026-1028 (2008).

Metzker,ML,"Sequencing Technologies—the Next Generation," Nature Review Genetics, 2010, 11:31-46.

Miller, Rich, "Who Has the Most Web Servers?" Data Center Knowledge, May 14, 2009 (http://www.datacenterknowledge.com/archives/2009/05/14/whos-got-the-most-web-servers/).

Perkel, Jeffrey M., "Sequence Analysis 101," The Scientist, Mar. 11, 2011 (http://www.the-scientist.com/?articles.view/articleNo/30731/title/Sequence- Analysis-101/).

Richter, Brent G., "Managing and Analyzing Next-Generation Sequence Data," PLOS Computational Biology, 5(6), Jun. 2009.

Soni & Meller, "Progress toward Ultrafast DNA Sequencing Using Solid-State Nanopores", Clin. Chern. 53:11, 1996-2001 (2007).

(56) References Cited

OTHER PUBLICATIONS

Stein, L., "The case for cloud computing in genome informatics," Genome Biology 2010,11:207.
Sundquist, Andreas, "DNAnexus free account: next-gen sequence analysis in the cloud," SEQanswers, Apr. 27, 2010 (http://seqanswers.com/forums/showthread.php?t=4877).
U.S. Appl. No. 13/790,596, filed Mar. 8, 2013, entitled: "Cloud Computing Environment for Biological Data", now U.S. Pat. No. 9,444,880.
Wu, Hao, "Intensity normalization improves color calling in SOLiD sequencing," Nat Methods. May 2010; 7(5): 336-337.

\* cited by examiner

FIG. 8

CLOUD COMPUTING ENVIRONMENT FOR BIOLOGICAL DATA

CROSS REFERENCE TO RELATED APPLICATIONS

This application is a division of U.S. patent application Ser. No. 16/259,434, filed Jan. 28, 2019, entitled "CLOUD COMPUTING ENVIRONMENT FOR BIOLOGICAL DATA", which is a continuation of U.S. patent application Ser. No. 15/258,651 (now patented as Ser. No. 10,223,502), filed Sep. 7, 2016, entitled "CLOUD COMPUTING ENVIRONMENT FOR BIOLOGICAL DATA", which is a continuation of U.S. patent application Ser. No. 13/790,596 (now patented as U.S. Pat. No. 9,444,880), filed Mar. 8, 2013, entitled "CLOUD COMPUTING ENVIRONMENT FOR BIOLOGICAL DATA", which claims priority from and the benefit of U.S. Provisional Application Ser. No. 61/622,763, filed Apr. 11, 2012, entitled "CLOUD COMPUTING ENVIRONMENT FOR BIOLOGICAL DATA", the disclosures of which are incorporated herein by reference in their entirety.

BACKGROUND

The present disclosure relates generally to the field of data related to biological samples, such a sequence data. More particularly, the disclosure relates to techniques for analyzing and/or storing data generated by a sequencing device in a cloud computing environment.

Genetic sequencing has become an increasingly important area of genetic research, promising future uses in diagnostic and other applications. In general, genetic sequencing involves determining the order of nucleotides for a nucleic acid such as a fragment of RNA or DNA. Relatively short sequences are typically analyzed, and the resulting sequence information may be used in various bioinformatics methods to logically fit fragments together to reliably determine the sequence of much more extensive lengths of genetic material from which the fragments were derived. Automated, computer-based examinations of characteristic fragments have been developed and have been used more recently in genome mapping, identification of genes and their function, and so forth. However, existing techniques are highly time-intensive, and resulting genomic information is accordingly extremely costly.

A number of alternative sequencing techniques are presently under investigation and development. In several techniques, typically single nucleotides or strands of nucleotides (oligonucleotides) are introduced and permitted or encouraged to bind to the template of genetic material to be sequenced. Sequence information may then be gathered by imaging the sites. In certain current techniques, for example, each nucleotide type is tagged with a fluorescent tag or dye that permits analysis of the nucleotide attached at a particular site to be determined by analysis of image data. Although such techniques show promise for significantly improving throughput and reducing the cost of sequencing, further progress in speed, reliability, and efficiency of data handling is needed.

For example, in certain sequencing approaches that use image data to evaluate individual sites, large volumes of image data may be produced during sequential cycles of sequencing. In systems relying upon sequencing by synthesis (SBS), for example, dozens of cycles may be employed for sequentially attaching nucleotides to individual sites. Images formed at each step result in a vast quantity of digital data representative of pixels in high-resolution images. These images are analyzed to determine what nucleotides have been added to each site at each cycle of the process. Other images may be employed to verify de-blocking and similar steps in the operations.

The image data is important for determining the proper sequence data for each individual site. While the image data may be discarded once the individual nucleotides in a sequence are identified, certain information about the images, such as information related to image or fluorescence quality, may be maintained to allow researchers to confirm base identification or calling. The image quality data in combination with the base identities for the individual fragments that make up a genome will become unwieldy as systems become capable of more rapid and large-scale sequencing. There is need, therefore, for improved techniques in the management of such data during and after the sequencing process.

BRIEF DESCRIPTION

The present disclosure provides a novel approach for shifting or distributing certain sequence data analysis features and sequence data storage to a cloud-based network. For example, the techniques relate to a cloud computing environment configured to receive data from one or more individual sequencing devices. In particular embodiments, the sequence data may be stored and/or analyzed using the cloud computing environment, which may reduce the processing and/or storage burden associated with the sequencing device itself or an associated computer. Sequencing devices represent significant capital investments for researchers, and a reduction in processing burden may result in a decreased cost per sequencing run. Further, because sequencing may be conducted at core laboratory facilities, the owner of the sequence data may not be local to the sequencing device. Storage of sequence data in a cloud computing environment as provided herein allows location-independent access and storage, as well as backup storage. Accordingly, high throughput facilities as well as smaller labs may have reduced memory requirements on-site for storing client data.

The cloud computing environment may also provide distributed processing for sequencing, allowing computing resources to be allocated to particular projects or users within the cloud computing environment. Such an implementation may allow small labs or clients to access advanced data processing platform at relatively lower costs, for example, on a pay-as-you-go basis. The cloud computing environment may also facilitate a virtual plug and play interaction between sequencing devices and data analysis platforms. That is, communication of the sequencing device and the cloud computing environment is relatively seamless and may be implemented without a great deal of IT support. Researchers may relinquish responsibility for servicing and updating devices running dedicated programs for analyzing sequence data, because maintenance of the data analysis software is conducted via the cloud monitoring systems. Such an arrangement frees up IT resources at the user or client site.

Certain public platforms for viewing sequence or gene-related data place no restrictions on the ability to view the data. However, in particular embodiments of the disclosure, the present techniques allow owners of sequence data to restrict access to the data. For example, the sequence data in the cloud may not be visible to anyone but the originator or owner of the data, may be shared selectively, or may be accessible to any authorized user of the cloud computing environment. Such conditional access may provide advantages for collaborators within a particular company. By storing and accessing sequence data within the cloud, collaborators at different locations may access data without setting up their own network or security systems. In one example, sequence data generated via a particular sequencing device may be uploaded to the cloud-based network and may be accessed by an approved list of researchers.

In addition, the cloud computing environment facilitates modification or annotation of sequence data by secondary users, which is in contrast to public platforms that only allow modification of sequence data by the original submitters of the data or the database administrators. For example, a primary user may be the owner of the sequence data, a researcher or clinician who uploads the sequence data to the cloud or an original researcher who performed the sequencing run. A secondary user may be any user who does not own the sequence data or, in particular embodiments, may be a user in a different research group within the same institution, in a different institution, or may be any other user. A secondary user may be, for example, a doctor or clinician who is handling a particular aspect of a patient's care. In one example, a primary user may authorize a select group of secondary users. In a particular embodiment, the group can include doctors or clinicians who are addressing a medical situation, including for example, a primary care physician, oncologist and genetic counselor who are caring for the individual whose sequence is being accessed. Members of the list may annotate or otherwise modify the sequence data, and the modifications may be stored with the sequence data such that accessing the sequence data calls up a full list of any annotations or modifications. Different users can have different permission levels with regard to the number and types of annotations they can make. Modification or annotation of sequence data within a cloud computing environment may allow researchers to apply third party analysis tools to sequences within the cloud with subsequent reporting of the results of the analysis in a location accessible to a desired group of users. Further, the cloud computing environment may be beneficial for providing a brokerage or swapping systems for completed genomes.

The present invention provides a system for analyzing biological samples, comprising: a cloud computing environment in communication with a plurality of sequencing devices, wherein the cloud computing environment comprises at least one server, the server being configured to communicate with a sequencing system remote from the server to receive and store sequence data from the sequencing system while the sequence data is being generated. The system may also include devices that are capable of providing data to the cloud computing environment, such as a sequencing module configured to generate the sequence data and a communications module configured to communicate the sequence data to the server.

The present invention also provides a computer implemented method for analyzing sequence data in a cloud computing environment, comprising: receiving, at a server, a request from a user to annotate sequence data stored on a cloud computing environment; determining if the user has permission to annotate the sequence data; modifying the sequence data based on an instruction related to an annotation if the user has permission to annotate the sequence data; and storing the sequence data with the annotation. The annotations may include information about the user and/or a quality rating of a previous annotation.

The present invention also includes a system for analyzing biological samples, comprising: at least one networked computer system configured to: receive sequence data from a remote sequencing device, wherein the sequence data comprises permissions for accessing the sequence data; receive a request from a secondary user to access the sequence data, the secondary user being different from the remote sequencing device; and allowing the secondary user access to the sequence data if the secondary user is authorized under the permissions. Such permissions may be defined by a primary user.

The present invention also includes a computer implemented method for providing genetic data, comprising: receiving, at a server, a request from a user for data related to a particular gene or set of genes on a cloud computing environment; monitoring, on the cloud computing environment, available data relating to the particular gene or set of genes; and conveying to the user the available data based upon the request.

The present invention also includes sequencing devices that are compatible with a cloud computing environment and that comprise: a module configured to acquire digitized signal data from a biological sample; at least one processor configured to: receive instructions to share data related to the biological sample with a cloud computing environment; receive the digitized signal data; determine nucleotide identities of the biological sample based on the digitized signal data; output one or more files comprising the nucleotide identities; and communicate the one or more files to a cloud computing environment while the module is acquiring additional digitized signal data from the biological sample.

The present invention also includes a system for analyzing biological samples, comprising: at least one processor configured to: request a first notification when sequence data comprising one or more parameters is uploaded to a cloud computing environment; receive a second notification related to a presence of new sequence data comprising the one or more parameters in the cloud computing environment; and request permission to view the new sequence data, wherein the new sequence data is generated from a remote sequencing device; a communications module configured to receive information related to the new sequence data; and a display configured to display the information related to the new sequence data.

The present invention also includes a system for analyzing biological samples, comprising: a cloud-based server in communication with a sequencing system and with a plurality of computer systems; a memory component that receives, via the server, genetic sequence data from the sequencing systems and stores the genetic sequence data; an analysis component configured to analyze the genetic sequence data and computing capacities of the computer systems; and a distribution component configured to distribute portions of the sequencing data to the plurality of computer systems based upon the analysis Embodiments of the present techniques are described herein by reference to sequencing data generated by a sequencing device. The disclosure is not, however, limited by the advantages of the aforementioned embodiment. The present techniques may also be applied to devices capable of generating other types of high throughput biological data, such as microarray data. Microarray data may be in the form of expression data, and the expression data may be stored, processed, and/or accessed by primary or secondary users in conjunction with the cloud computing environment as provided herein.

DRAWINGS

FIG. 8 is an example of a display screen of a user interface for setting the analysis parameters for sequence data according to the flow diagram of FIG. 7;

DETAILED DESCRIPTION

Figure 1:
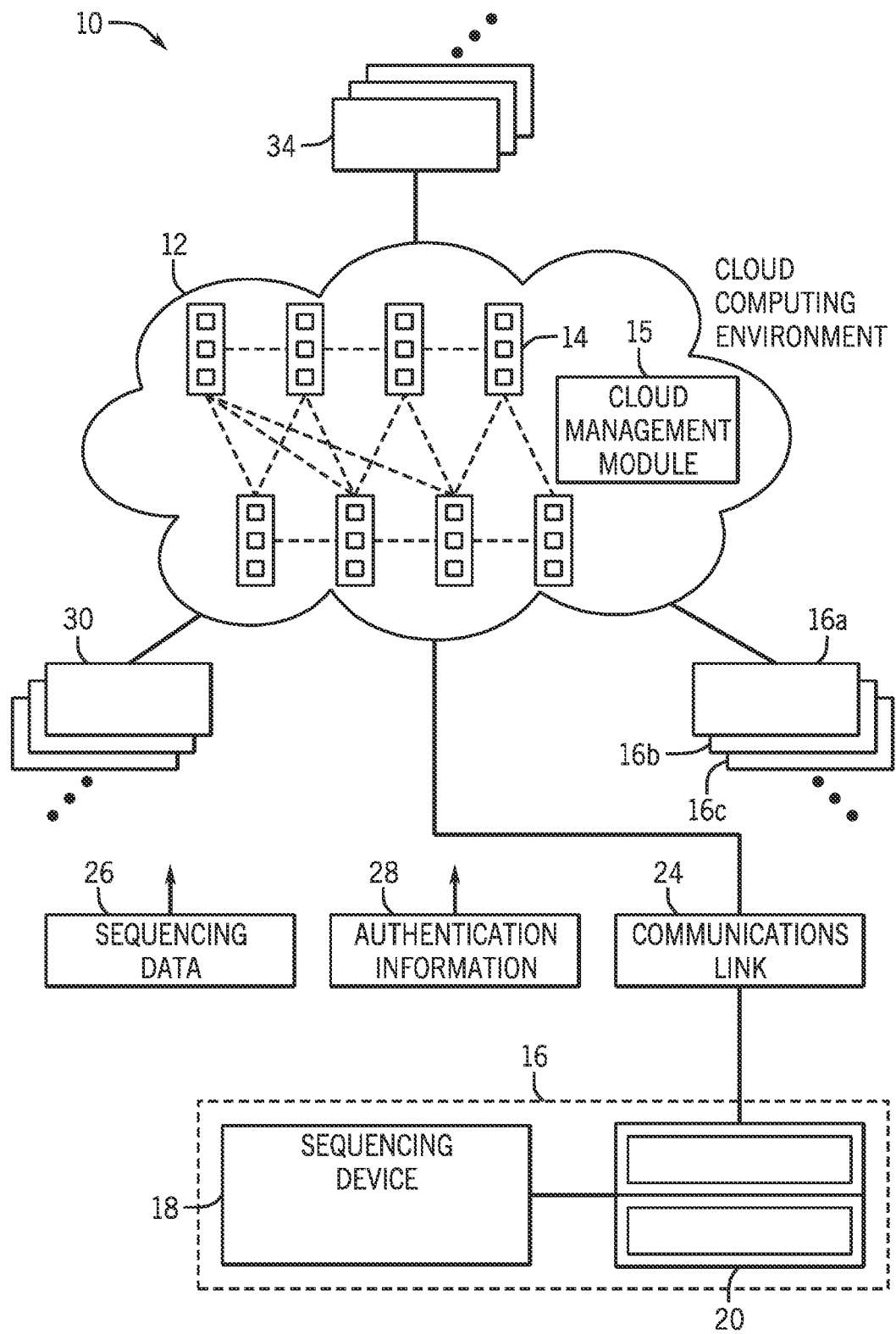
FIG. 1 is a diagrammatical overview for a system incorporating a cloud computing environment in accordance with the present invention.

Turning now to the drawings, and referring first to FIG. 1, a cloud computing environment 10 for biological data is illustrated diagrammatically. As used herein, the term "cloud" or "cloud computing environment" may refer to various evolving arrangements, infrastructure, networks, and the like that will typically be based upon the Internet. The term may refer to any type of cloud, including client clouds, application clouds, platform clouds, infrastructure clouds, server clouds, and so forth. As will be appreciated by those skilled in the art, such arrangements will generally allow for use by owners or users of sequencing devices, provide software as a service (SaaS), provide various aspects of computing platforms as a service (Paas), provide various network infrastructures as a service (IaaS) and so forth. Moreover, included in this term should be various types and business arrangements for these products and services, including public clouds, community clouds, hybrid clouds, and private clouds. Any or all of these may be serviced by third party entities. However, in certain embodiments, private clouds or hybrid clouds may allow for sharing of sequence data and services among authorized users.

The cloud computing environment 12 includes a plurality of distributed nodes 14. The computing resources of the nodes 14 are pooled to serve multiple consumers, with different physical and virtual resources dynamically assigned and reassigned according to consumer demand. Examples of resources include storage, processing, memory, network bandwidth, and virtual machines. The nodes 14 may communicate with one another to distribute resources, and such communication and management of distribution of resources may be controlled by a cloud management module 15, residing one or more nodes 14. The nodes 14 may communicate via any suitable arrangement and protocol. Further, the nodes 14 may include servers associated with one or more providers. For example, certain programs or software platforms may be accessed via a set of nodes 14 provided by the owner of the programs while other nodes 14 are provided by data storage companies. Certain nodes 14 may also be overflow nodes that are used during higher load times.

In one embodiment, the cloud management module 15 is responsible for load management and cloud resources. The load management may be implemented through consideration of a variety of factors, including user access level and/or total load in the cloud computing environment 12 (peak times versus average load times). The project type may also be considered. In one embodiment, public health emergencies may be prioritized over other types of projects. Further, a user may manage costs by offering certain runs as lower priority that are held until cloud usage is below a certain threshold.

The cloud computing environment 12 is configured to communicate with various users, including users of devices for generating biological data. Such data may include sequence data generated via a sequencing device 16, which in particular embodiments may include a device 18 that includes a module to accept a biological sample and generate sequence data and an associated computer 20 that includes executable instructions for analyzing or communicating the sequence data to the cloud computing environment 12. It should be understood that, in certain embodiments, the sequencing device 16 may also be implemented as an all-in-one device. The sequencing device 16 is configured to communicate with the cloud computing environment 12 via a suitable communications link 24. The communication with the cloud computing environment 12 may include communication via a local area network (LAN), a general wide area network (WAN), and/or a public network (e.g., the Internet) via the communications link 24. In particular, the communications link 24 sends sequence data 26 and, in certain embodiments, authentication information 28, to the cloud computing environment 12. The authentication information may confirm that the sequencing device 16 is a client of the cloud computing environment 12.

As noted, the cloud computing environment 12 may serve multiple users or clients with associated devices, e.g., devices 16a, 16b, and 16c. Further, the cloud computing environment 12 may also be accessed by other types of clients, such as secondary users 30 or third party software holders 34. Accordingly, the cloud computing environment 12 may provide different types of services depending on the access level of the particular client. A sequencing client may have access to storage and data analysis services, while a secondary user 30 may have access only to shared or public sequences. Third party software holders 34 may negotiate with sequencing clients to determine appropriate access privileges. For example, open source software may be offered for free or on limited license basis, while other types of software may be offered according to various fee or subscription bases.

Figure 2:
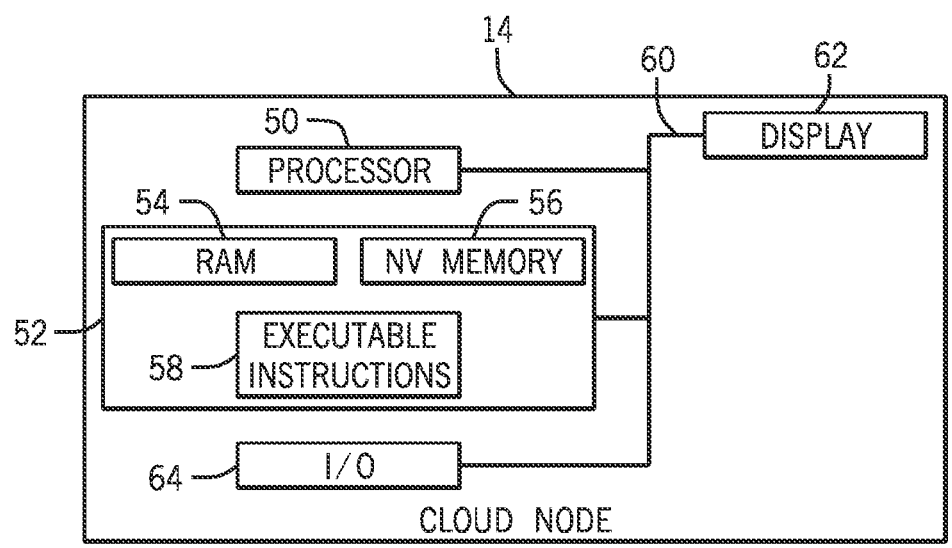
FIG. 2 is a diagrammatical overview of an individual node of the cloud computing environment of the type discussed with reference to FIG. 1.

FIG. 2 is a schematic diagram of an implementation of an individual node 14 of the cloud computing environment 12. The node 14 may be implemented as one or more of a personal computer system, server computer system, thin client, thick client, hand-held or laptop device, multiprocessor system, microprocessor-based system, set top box, programmable consumer electronic, network PC, minicomputer system, mainframe computer system, and distributed cloud computing environments 12 that include any of the above systems or devices, and the like. The node 14 may include one or more processors or processing units 50, a memory architecture 52 that may include RAM 54 and non-volatile memory 56. The memory architecture 52 may further include removable/non-removable, volatile/non-volatile computer system storage media. Further, the memory architecture 52 may include one or more readers for reading from and writing to a non-removable, non-volatile magnetic media, such as a hard drive, a magnetic disk drive for reading from and writing to a removable, non-volatile magnetic disk (e.g., a "floppy disk"), and/or an optical disk drive for reading from or writing to a removable, non-volatile optical disk such as a CD-ROM, DVD-ROM. The node 14 may also include a variety of computer system readable media. Such media may be any available media that is accessible by the cloud computing environment, such as volatile and non-volatile media, and removable and non-removable media.

The memory architecture 52 may include at least one program product having a set (e.g., at least one) of program modules implemented as executable instructions that are configured to carry out the functions of the present techniques. For example, executable instructions 58 may include an operating system, one or more application programs, other program modules, and program data. Generally, program modules may include routines, programs, objects, components, logic, data structures, and so on, that perform particular tasks or implement particular abstract data types. Program modules may carry out the functions and/or methodologies of the techniques as described herein including, but not limited to, primary sequence data analysis and secondary sequence analysis.

The components of the node 14 may be coupled by an internal bus 60 that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The node 14 may also communicate with one or more external devices such as a keyboard, a pointing device, a display 62, etc.; that enable a user to interact with the cloud computing environment 12; and/or any devices (e.g., network card, modem, etc.) that enable node 14 to communicate with one or more other computing devices. Such communication can occur via I/O interfaces 64. Still yet, the nodes 14 of the cloud computing environment 12 may communicate with one or more networks such as a local area network (LAN), a general wide area network (WAN), and/or a public network (e.g., the Internet) via a suitable network adapter.

Figure 3:
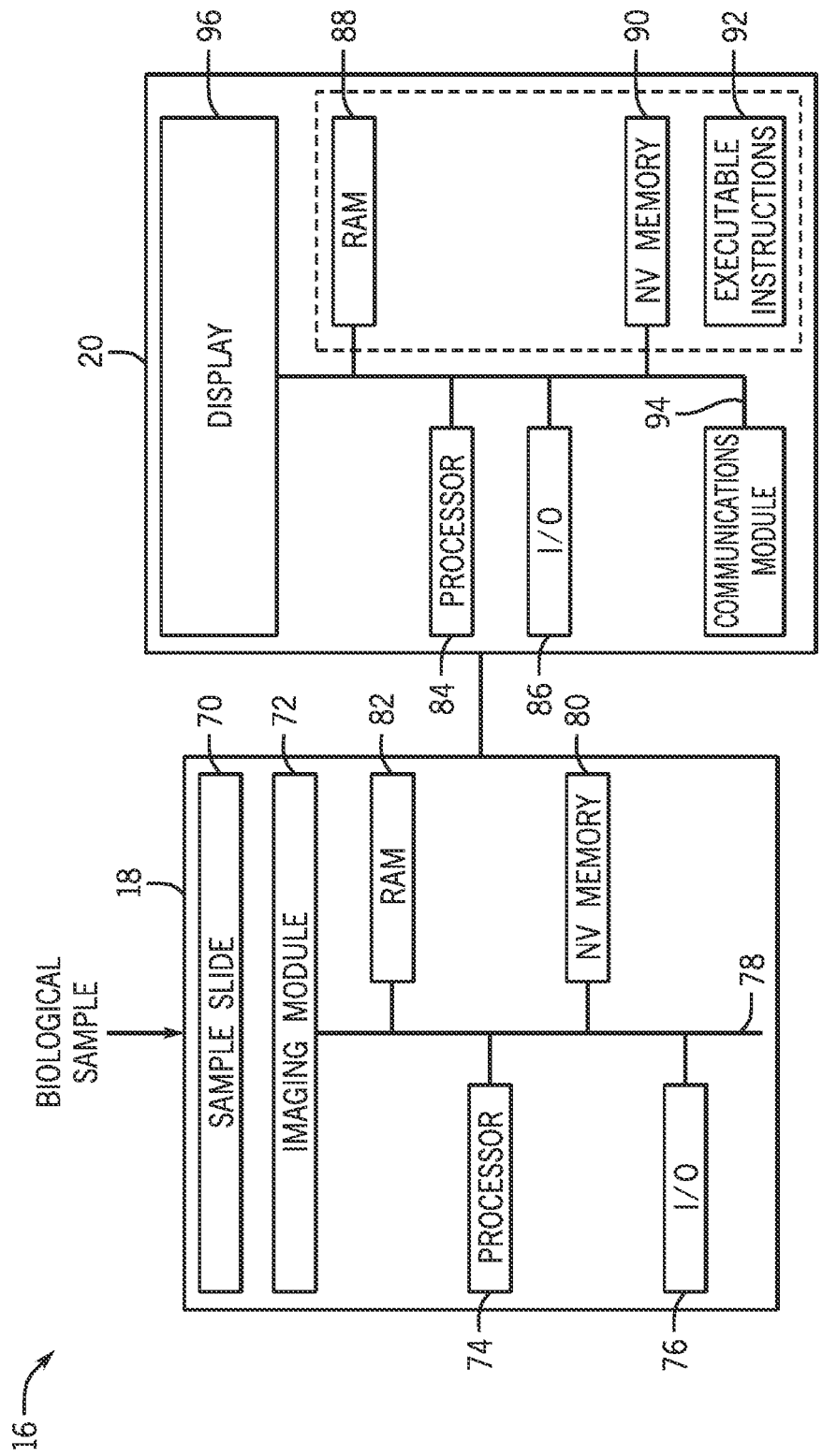
FIG. 3 is a diagrammatical overview of a biological sample processing system that may be used in conjunction with the cloud computing environment of the type discussed with reference to FIG. 1.

FIG. 3 is a schematic diagram of the sequencing device 16 that may be used in conjunction with the cloud computing environment 12. The sequence device 16 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 16. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, Clin. Chem. 53, 1996-2001 (2007); Healy, Nanomed. 2, 459-481 (2007); and Cockroft, et al. J. Am. Chem. Soc. 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides as described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 16 may be a HiSeq, MiSeq, or HiScanSQ from Illumina (La Jolla, CA).

In the depicted embodiment, the sequencing device 16 includes a separate sample processing device 18 and an associated computer 20. However, as noted, these may be implemented as a single device. Further, the associated computer 20 may be local to or networked with the sample processing device 18. In other embodiments, the computer 20 may a cloud computing environment access device that is remote from the sequencing device 16. That is, the computer 20 may be capable of communicating with the sequencing device 16 through the cloud computing environment 12. In the depicted embodiment, the biological sample may be loaded into the sample processing device 18 as a sample slide 70 that is imaged to generate sequence data. For example, reagents that interact with the biological sample fluoresce at particular wavelengths in response to an excitation beam generated by an imaging module 72 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics 26. This retrobeam may generally be directed toward detection optics of the imaging module 72.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 72 may be under processor control, e.g., via a processor 74, and the sample receiving device 18 may also include I/O controls 76, an internal bus 78, non-volatile memory 80, RAM 82 and any other memory structure such that the memory is capable of storing executable instructions, and other suitable hardware components that may be similar to those described with regard to FIG. 2. Further, the associated computer 20 may also include a processor 84, I/O controls 86, a communications module 87, and a memory architecture including RAM 88 and non-volatile memory 90, such that the memory architecture is capable of storing executable instructions 92. The hardware components may be linked by an internal bus 94, which may also link to the display 96. In embodiments in which the sequencing device is implemented as an all-in-one device, certain redundant hardware elements may be eliminated.

Further, a primary user (or secondary user) may also interact with the cloud computing environment 12 through any appropriate access device, such as a general purpose computer or mobile device that includes components similar to those described with regard to the computer 20. That is, once the sequence data has been communicated to the cloud computing environment 12, further interaction with and access to the sequence data may not necessarily be coupled to the sequence device 16. Such embodiments may be beneficial in embodiments in which the owner of the biological sample and/or sequence data has contracted for sequencing, e.g., to a core laboratory facility. In such embodiments, the primary user may be the owner while the core laboratory facility associated with the sequencing device 16 is at most a secondary user after the sequence data has been communicated to the cloud computing environment 12. In certain embodiments, the sequence data may be accessed through security parameters such as a password-protected client account in the cloud computing environment 12 or association with a particular institution or IP address. The sequence data may be accessed by downloading one or more files from the cloud computing environment 12 or by logging into a web-based interface or software program that provides a graphical user display in which the sequence data is depicted as text, images, and/or hyperlinks. In such an embodiment, the sequence data may be provided to the primary or secondary user in the form of data packets transmitted via a communications link or network.

The cloud computing environment 12 may execute user interaction software (e.g., via a web-based interface or application platform) that provides a graphical user interface for users and that facilitates access to sequence data, a community or group of researchers, data analysis programs, available third party software, and user selections for load balancing and instrument settings. For example, in particular embodiments, settings for a sequencing run on a sequencing device 16 may be set via the cloud computing environment 12. Accordingly, the cloud computing environment 12 and an individual sequencing device 16 may be capable of two-way communication. Such an embodiment may be particularly useful for controlling parameters of a remote sequencing run.

Figure 4:
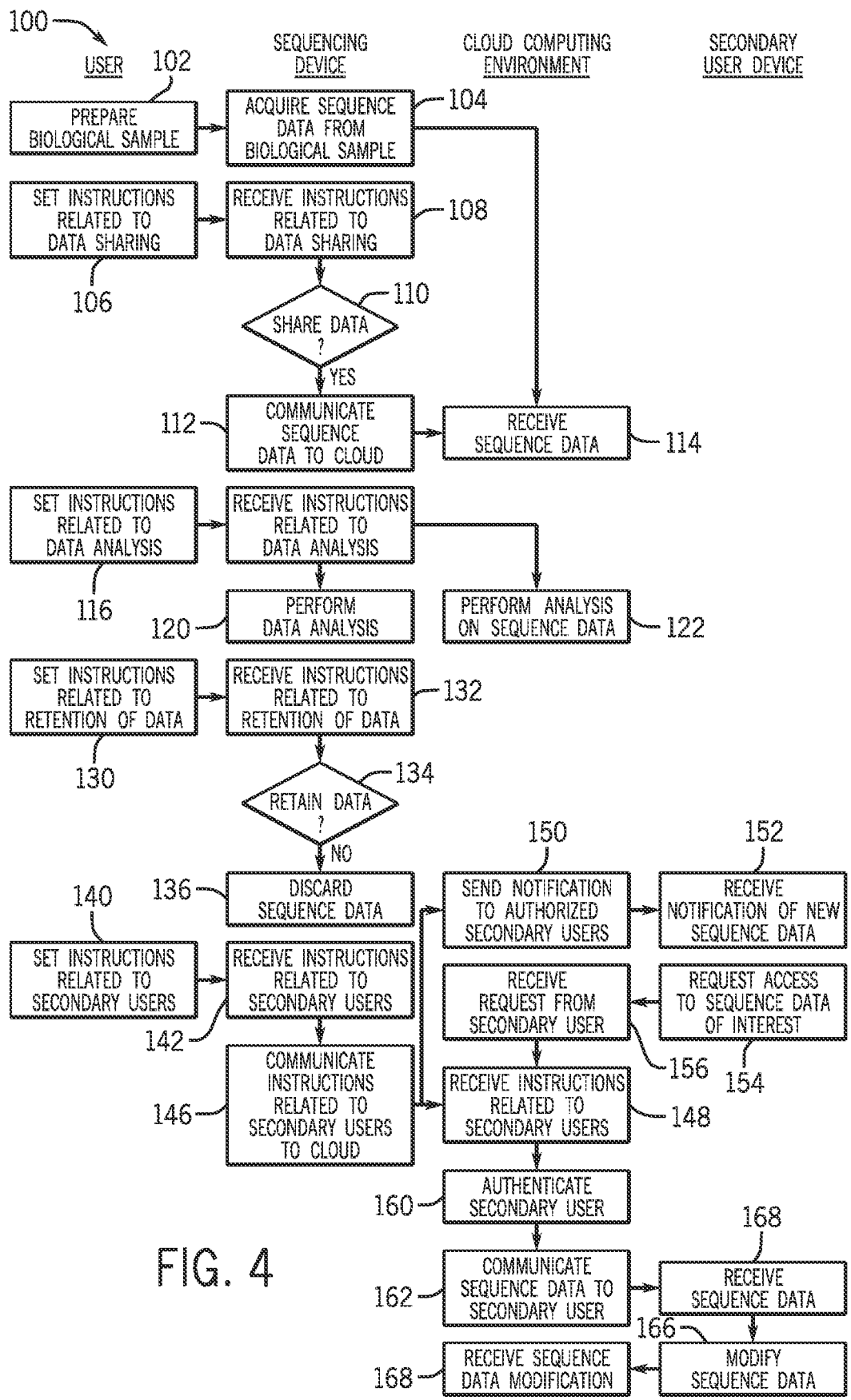
FIG. 4 is a flow diagram of a method of interaction between a primary user of a sequencing device, the cloud computing environment, and one or more secondary users that may be performed in conjunction with the system discussed with reference to FIG. 1.

As provided herein, the system 10 facilitates the interaction of users of sequencing devices 16 and/or owners of sequencing data with the cloud computing environment 12 and collaborators or secondary users (e.g., secondary users 30). To that end, FIG. 4 is a flow diagram of the pathways of some exemplary interactions. The method 100 may encompass any viable subset or combination of the steps or interactions depicted. In one embodiment, the method 100 may begin with preparing a biological sample at block 102. The sequencing device 16 acquires sequence data from the biological sample at block 104. Depending on the settings on the sequencing device, the sequence data may be uploaded to the cloud computing environment 12. For example, in one embodiment, the user may set the sequence data sharing settings at block 106, which is received by the sequencing device at block 108. When the sequence data is acquired (at block 104), the sequencing device 16 determines at block 110 if the settings are consistent with sharing the sequence data. If so, the sequence data is communicated from the sequence device 16 to the cloud computing environment 12, which receives the sequence data at block 114. The shared sequence data in the cloud computing environment 12 may be stored or further processed.

As discussed with regard to FIG. 1, the cloud computing environment 12 is capable of analyzing sequence data. A user may set parameters for data analysis in the cloud computing environment 12 at block 116 that are received by the sequencing device at step 118 before starting a sequencing run. For example, the user may indicate which analyses are to be performed locally (i.e., at the sequencing device 16) and which are to be performed in the cloud computing environment 12. In one embodiment, the cloud computing environment 12 may provide feedback or resource information to the sequencing device 16. For example, the cloud computing environment 12 may provide an estimate of a time for a particular analysis, e.g., genome assembly, based on available processing resources and scheduled tasks. The user may then set the parameters based on the information. The data analysis may be performed locally (at block 120) or in the cloud (at block 122). In one embodiment, the parameters may be set such that primary analysis (e.g., base identification) is performed locally while secondary analysis (e.g., genome assembly) is performed in the cloud computing environment 12.

The system 10 also provides techniques for reducing data storage requirements on the sequencing device 16. For example, a user may set instructions relating to retention of the sequence data (block 130) that are received by the sequencing device 16 (block 132). As the sequence data is acquired, the sequencing device 16 may check to determine if instructions were received to retain the acquired data (block 134) and determine if the sequence data is to be discarded (block 136).

The system 10 also provides techniques for notifying or authorizing secondary users that include instructions that may be set by the user (block 140) and received at the sequencing device 16 (block 142). If the instructions indicate that the sequence data is to be shared with one or more secondary users, the instructions are communicated (block 146) by the sequencing device 16 and received (block 148) by the cloud computing environment 12. The access is then implemented according to the instructions. For example, if the instructions include a notification provision, a notification is sent (block 150) to the secondary user, which may be received (block 152) in the form of an email or message in a cloud computing account, for example.

In other embodiments, the sequence data access instructions may also set permissions for at least partial access by a secondary user who sends a request (block 154) to access the sequence data that is received by the cloud computing environment (block 156). The request is authenticated based on the instructions at block 160 and the sequence data is communicated to the secondary user at block 162. The secondary user may access or receive the sequence data (block 164) in the form of a downloaded file or may access the sequence data via a web-based interface or a software package. If the permissions governing secondary user access to the sequence data allow modification or annotation of the sequence data, a modification created by the secondary user (block 166) may be received by the cloud computing environment (block 168). The modification may be stored as part of the sequence data, such that subsequent users may view the modification. Modifications may include annotations, such as structural or functional annotations, or comments or questions related to the sequence data.

Figure 5:
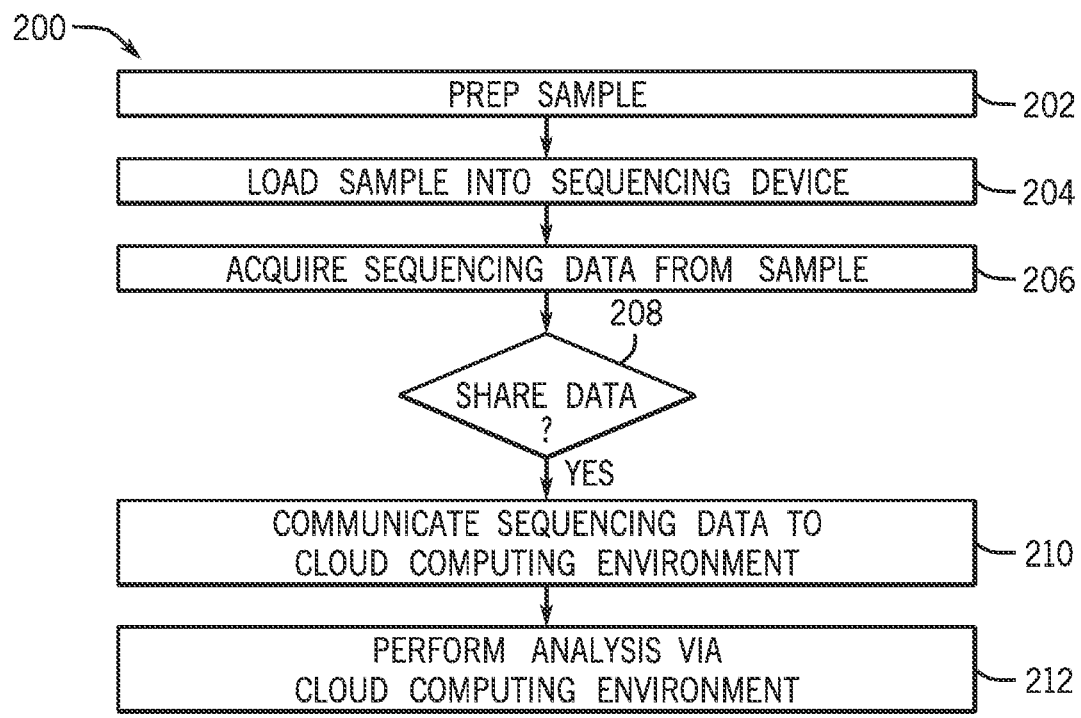
FIG. 5 is a flow diagram of a method of providing sequence data to the cloud computing environment of the type discussed with reference to FIG. 1.

FIG. 5 is a flow diagram of one implementation of a method 200 of generating and sharing sequence data with the cloud computing environment 12 with a sequencing device 16. For example, a user may prepare a biological sample at block 202 according to a desired sequencing protocol and load the sample into the sequencing device 16 at block 204. It should be understood that, in particular embodiments, a sample may be loaded into the sequencing device 16 with no preparation and/or may be automatically loaded with no user intervention. For example, a biological sample may be automatically loaded into a cartridge that includes appropriate reagents for preparing the sample for bridge amplification. The sequence data is acquired at block 206. The sequencing device 208 at decision block 208 checks against stored instructions to determine if the sequence data is to be shared with the cloud computing environment 12. If the stored instructions indicate that the sequence data is to be shared, the sequencing device 16 communicates the sequence data to the cloud computing environment 12 at block 210. At step 212, the sequence data is analyzed in the cloud computing environment according to user instructions.

Figure 6:
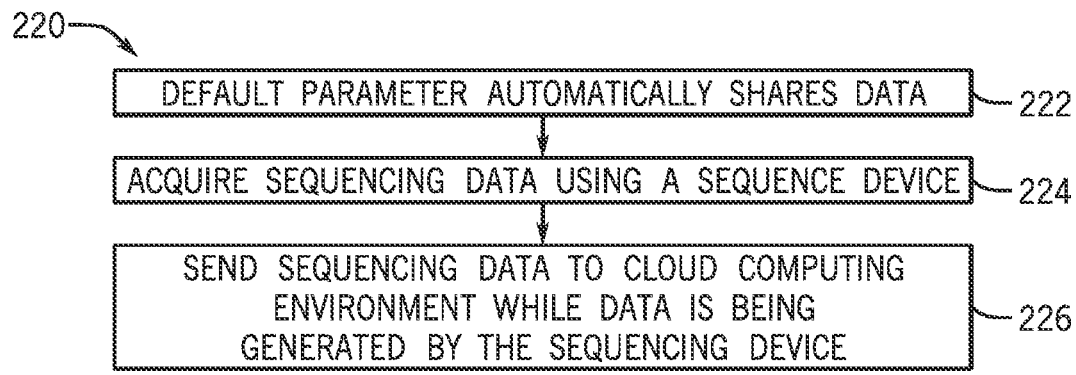
FIG. 6 is a flow diagram of a method of providing sequence data to the cloud computing environment of the type discussed with reference to FIG. 1.

FIG. 6 is a flow diagram of a method 220 of default sequence data sharing in which the sequencing device at step 222 is set to automatically share sequence data when the sequence data is acquired at step 224. In such an embodiment, the data sharing occurs with no positive action from the user, i.e., the sharing involves no change in parameters from the default. Further, if desired, the user may actively change the default settings such that the sequence data is not sent to the cloud computing environment 12. Accordingly, at step 226, the sequence data generated by the sequence device 16 is sent to the cloud computing environment while the data is being generated. For example, such data may include optical image data acquired from the imaging module 72. The partial images of the sample slide 70 may be automatically uploaded to the cloud computing environment 12 as each image or series of images is acquired. Digitized signal data of other types (besides image based data) can be similarly processed as appropriate for the particular data format. The cloud computing environment 12 may perform primary analysis on any of a variety of types of digitized signal data including, but not limited to, image data that is digitized. In other embodiments, the digitized signal data may undergo at least partial primary analysis before being sent to the cloud computing environment 12. In such embodiments, the digitized signal data may be converted to files that include base identities (i.e., base calls) for individual reads and, optionally, associated data quality assessments before being send to the cloud computing environment 12.

In one embodiment of the present techniques, the sequence data is sent to the cloud computing environment 12 as the sequence data is generated, for example in real-time. In the case of raw image data, an image file may be sent as soon as the image is acquired. In the case of sequence data that undergoes processing on the sequencing device, the sequence data may be sent as soon as a base call file is generated. Because a sequencing run generally includes multiple base call files, the files may be sent to the cloud computing environment 12 on a rolling basis. Accordingly, a portion of the sequence data may already be uploaded to the cloud computing environment 12 while the sequencing run is still ongoing. In other embodiments, the sequence data is uploaded to the cloud after the sequencing run is complete. In particular embodiments, the data generated on the device 16 may be automatically discarded after the sequence data is sent to the cloud computing environment 12. This discarding step may reduce the memory and processing requirements for an individual sequencing device 16.

Figure 7:
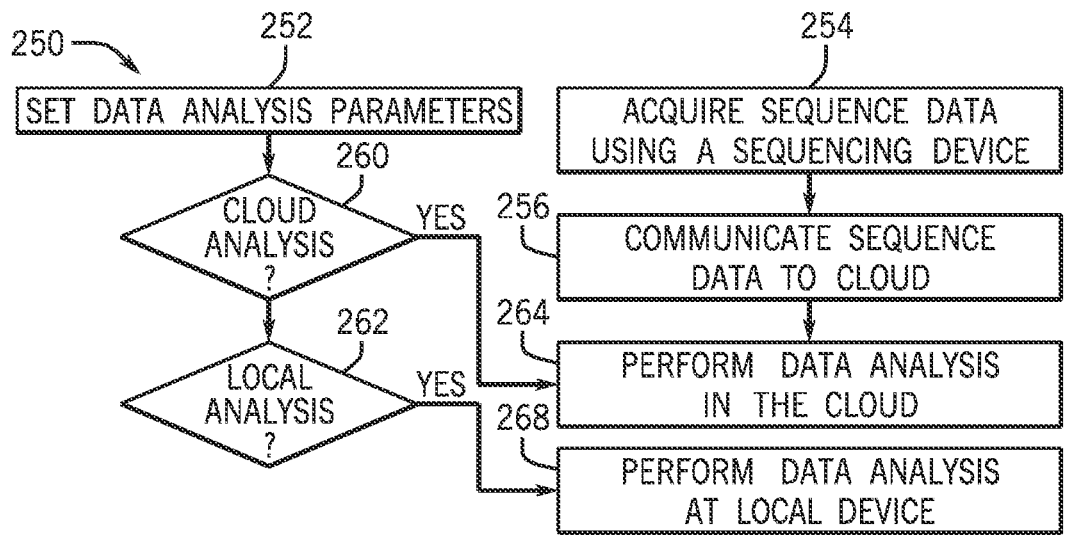
FIG. 7 is a flow diagram of a method of setting analysis parameters for sequence data in the cloud computing environment of the type discussed with reference to FIG. 1.

FIG. 7 is a flow diagram of a method 250 for performing distributed data analysis in the cloud computing environment 12. At step 252, the user sets the data analysis parameters at the sequence device 16, which acquires the sequence data (block 254) and communicates the sequence data to the cloud computing environment (block 256). Such parameters may include whether the analysis takes place in the cloud computing environment (block 260) and/or locally (block 262). In particular, the techniques provided herein facilitate efficient distribution of computing resources. If the local device (e.g., the computer 20 associated with the sequencing device 16) has available resources, it may be more efficient to perform at least primary analysis locally. In other embodiments, the user may elect to perform data analysis in the cloud as well as locally. Once the sequence data is acquired and communicated to the cloud computing environment 12, the selected analysis is performed (block 264) in the cloud. If the user has elected to perform local analysis, the sequence data is retained locally so that such analysis may take place (block 268).

Figure 8:
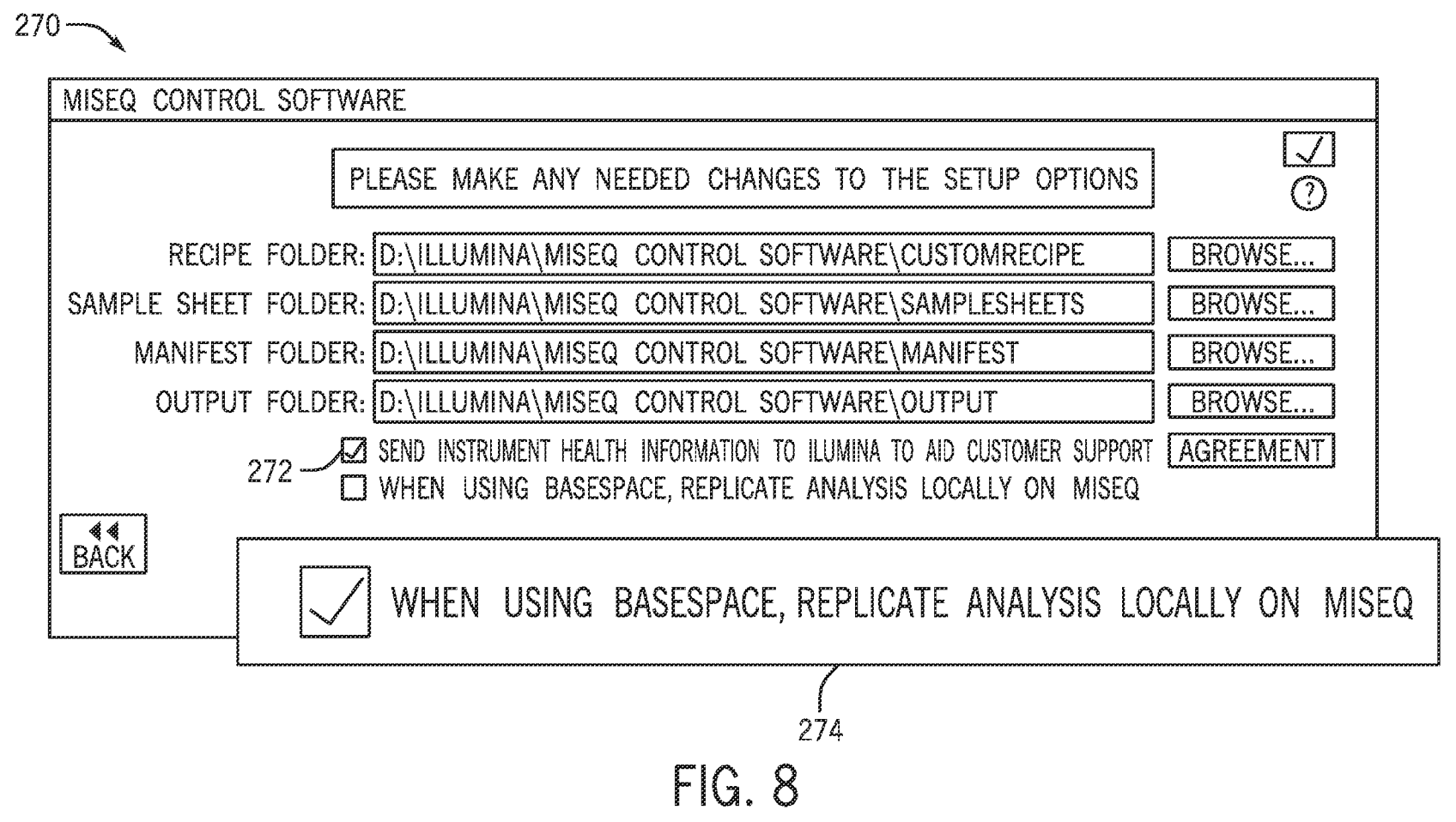

FIG. 8 is an example of a graphical display screen 270 for selecting setup options for a sequencing run performed on the sequencing device 16. The graphical display screen 270 may be viewed on the sequencing device 16 or may be viewed on a separate device (e.g., a general purpose computer or mobile device having features as discussed with regard to FIG. 3) that accesses or communicates with the cloud computing environment 12. The graphical display screen 270 may include selectable menu options for uploading data to the cloud computing environment 12. In addition to sequence data, the sequencing device 16 may provide data to the cloud computing environment 12 that is related to a condition of the sequencing device 16. A selectable menu item 272 is an example of such a setup option. For example, the sequencing device may perform a periodic diagnostic test, and the results of the test may be automatically uploaded to the cloud computing environment 12, regardless of whether the user has indicated that the sequence data will be shared. That is, condition information may be sent with or without sequence data to the cloud computing environment 12. In one embodiment, the diagnostic test may include information about a number of sequencing runs, which may be linked to scheduled maintenance or may be used to schedule delivery of or reminders related to reagent supplies. In another embodiment, the diagnostic information may include a check for bugs or other errors. Accordingly, the information may be set to be shared with the manufacturer of the sequencing device 16. Further, the diagnostic test may include a check for software updates. In such an embodiment, the cloud computing environment 12 may be configured to automatically provide any relevant software updates to the sequencing device 16 via the communications link 24. The diagnostic test may also include information that may be provided to the manufacturer of the device to facilitate software development, such as information about the most commonly used sequencing parameters.

In addition, the selectable menu options may include an option to perform local analysis 274. That is, any data analysis performed on the sequence data is replicated on the sequencing device 16. Such an embodiment may be beneficial when the data shared in the cloud computing environment 12 includes public annotations while the local data includes annotations with patient-specific information or private annotations.

The data retention and compression features facilitated by the cloud computing environment 12 may allow originators of data to manage the large data sets created through sequencing techniques. For example, over time, the sequence data set size may increase much faster than typical internet access speeds. In such embodiments, the sequencing device 16 may compress the sequence data prior to transmission to the cloud computing environment 12. Algorithms for sequence compression, e.g. "CRAM"-style techniques, may be executed by a processor associated with the sequencing device 16 to compress the sequence data.

Certain compression algorithms, while effective, are also "lossy" in that they throw away some data resolution. Accordingly, certain users may wish to use the compression algorithms, while other users may elect to store the sequence data in an uncompressed state to retain the highest level of data resolution. In certain embodiments, the setup options for a sequencing run may also offer a "compress after primary analysis" menu option associated with each sequence data set stored on the cloud. In other embodiments, a user interface associated with the cloud computing environment may provide data compression as a menu option. In such embodiments, the setup options for a sequencing run may also offer a "compress now" menu option associated with each sequence data set stored on the cloud. Users that have large uncompressed data sets stored can select this option to get a particular data set compressed, providing for example 50× reduction in cost for saving that particular data set.

Figure 9:
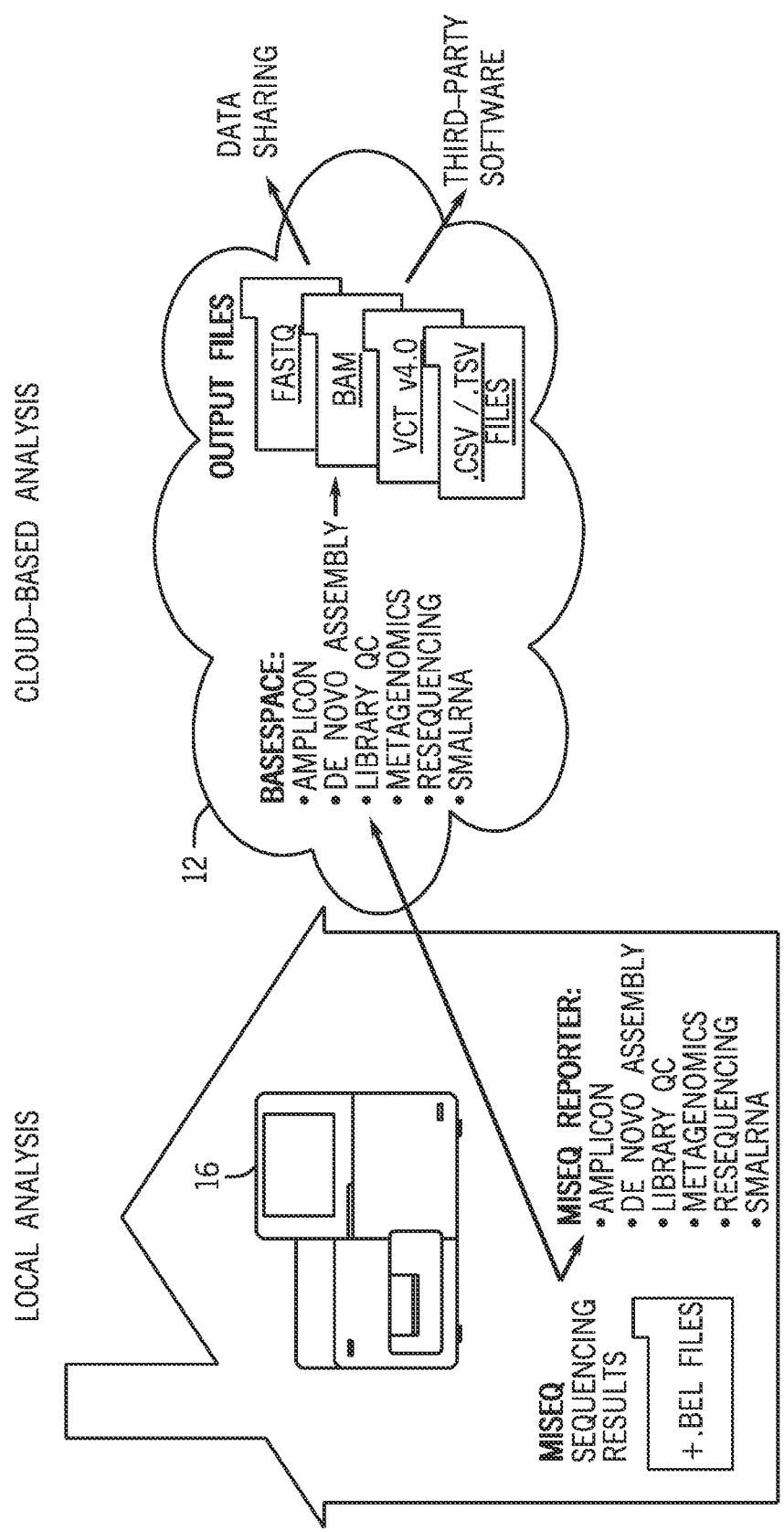
FIG. 9 is a schematic overview of data analysis performed at a sequencing device and in the cloud computing environment of the type discussed with reference to FIG. 1.

FIG. 9 is a schematic diagram of an example of local data and cloud-based analysis options. In the depicted embodiment, the sequencing device 16 generates sequencing data as base call files. Both the sequencing device 16 and the cloud computing environment 12 are capable of processing the base call files to perform Amplicon, de novo assembly, Library QC, metagenomics, resequencing, and smallRNA discovery. Other types of data analysis may include clinical analysis, such as GeneInsight. In particular embodiments, the data analysis may be performed according to industry or regulatory agency standards, such as CLIA.

The files generated from the various analyses may take the form of FASTQ files, binary alignment files (bam) *.bcl, *.vcf, and/or *.csv files. The output files may be in formats that are compatible with available sequence data viewing, modification, annotation, and manipulation software. Accordingly, the accessible sequence data as provided herein may be in the form of raw data, partially processed or processed data, and/or data files compatible with particular software programs. Further, the output files may be compatible with other data sharing platforms or third party software.

Figure 10:
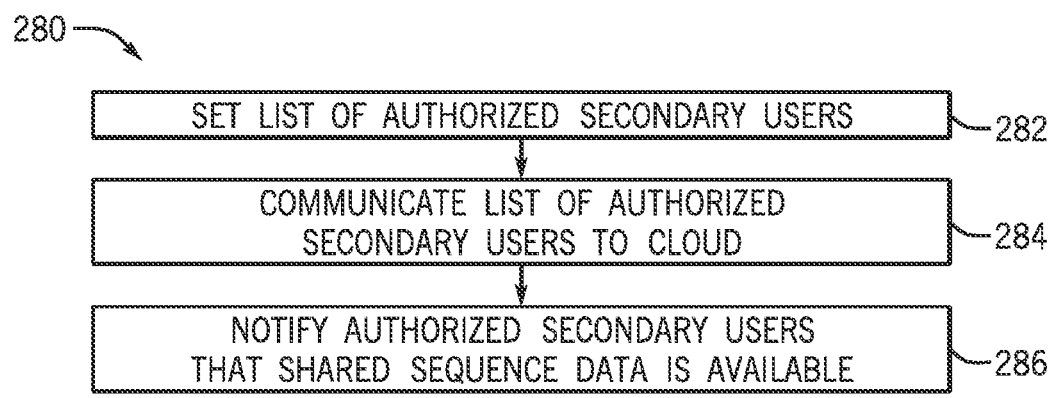
FIG. 10 is a flow diagram of a method of authorizing secondary users to access sequence data in the cloud computing environment of the type discussed with reference to FIG. 1.

FIG. 10 is a flow diagram of a method 280 of authorizing secondary users. The setup options for a new sequencing run may include the option to set any authorized secondary users at block 282. The instructions may be communicated to the cloud computing environment 12 at block 284, either separately or together with the acquired sequence data. The cloud computing environment may then notify the authorized secondary users of the presence of the new sequencing data at block 286.

Figure 11:
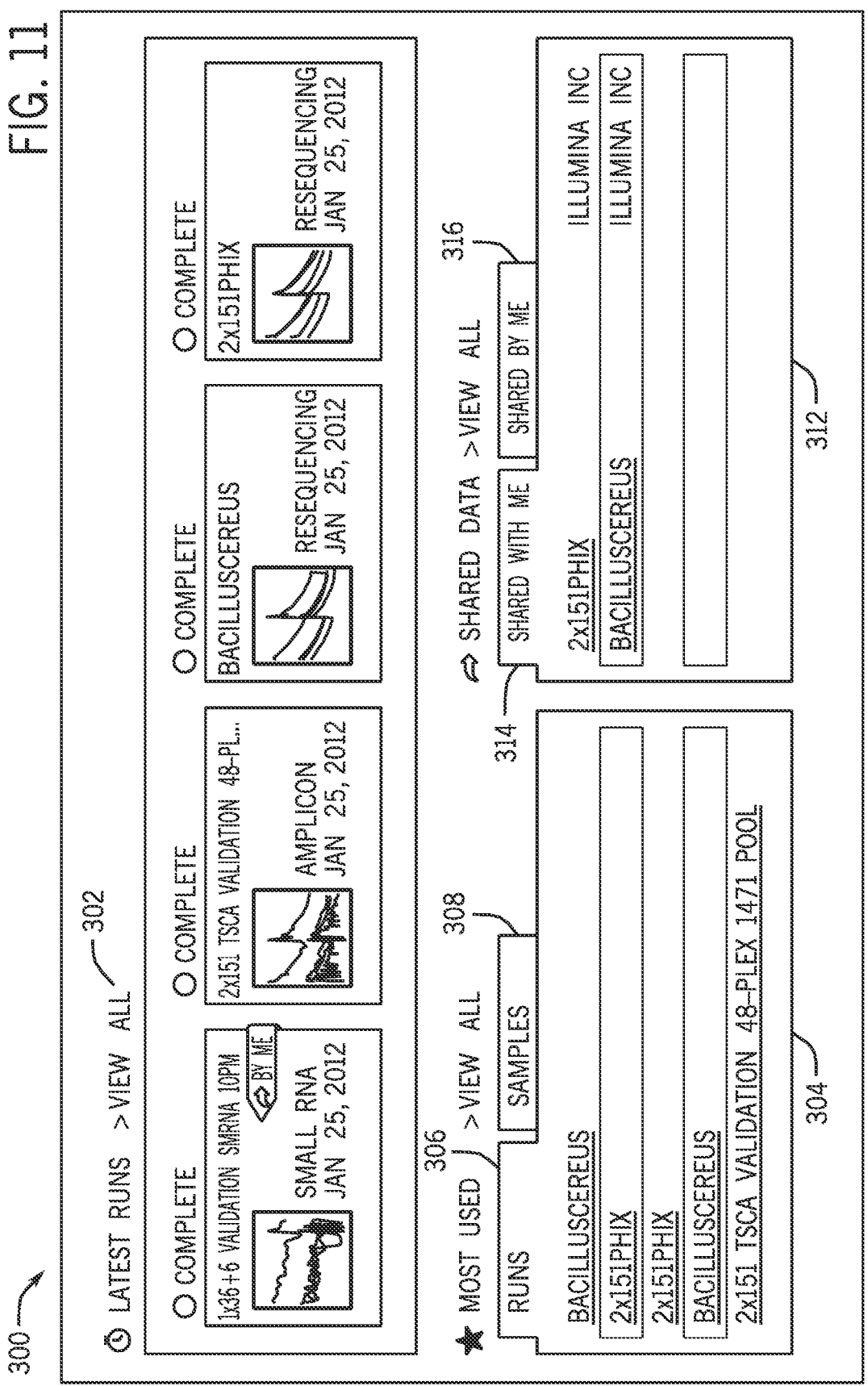
FIG. 11 is an example of a display screen of a user interface for showing shared sequence data.

For example, the notification may take the form of indicating that new sequences are available in an account running on a user device and connected to the cloud computing environment 12. FIG. 11 is an example of a display screen 300 facilitated by software instructions executed on the cloud computing environment 12 and viewed on a primary user or secondary user cloud access device (e.g., a general purpose computer, a mobile device, or the sequencing device 16 running software for interacting with the cloud computing environment 12). The display screen 300 may be part of the data viewing platform provided by the cloud computing environment 12. The depicted display screen 300 may be a higher level summary of sequence data available to the user. For example, the display screen includes linked icons 302 for available sequencing runs, including identifying information, the run type (e.g., small RNA, Amplicon), and/or whether the run is a primary run (by the user) or a secondary run (by another). The cloud computing environment 12 may provide notification of which runs are new since the last login. Selecting the icons accesses the sequence data associated with a particular sequencing run. Other panels of the display screen may provide tabs for most-used links 304, such as accessed runs 306 or accessed samples 308. A sharing panel 312 includes a tab 314 for data shared with the user and a separate tab 316 for data shared by the user. Other display screens that may be viewed on the user access device may include setup options or load balancing options.

Figure 12:
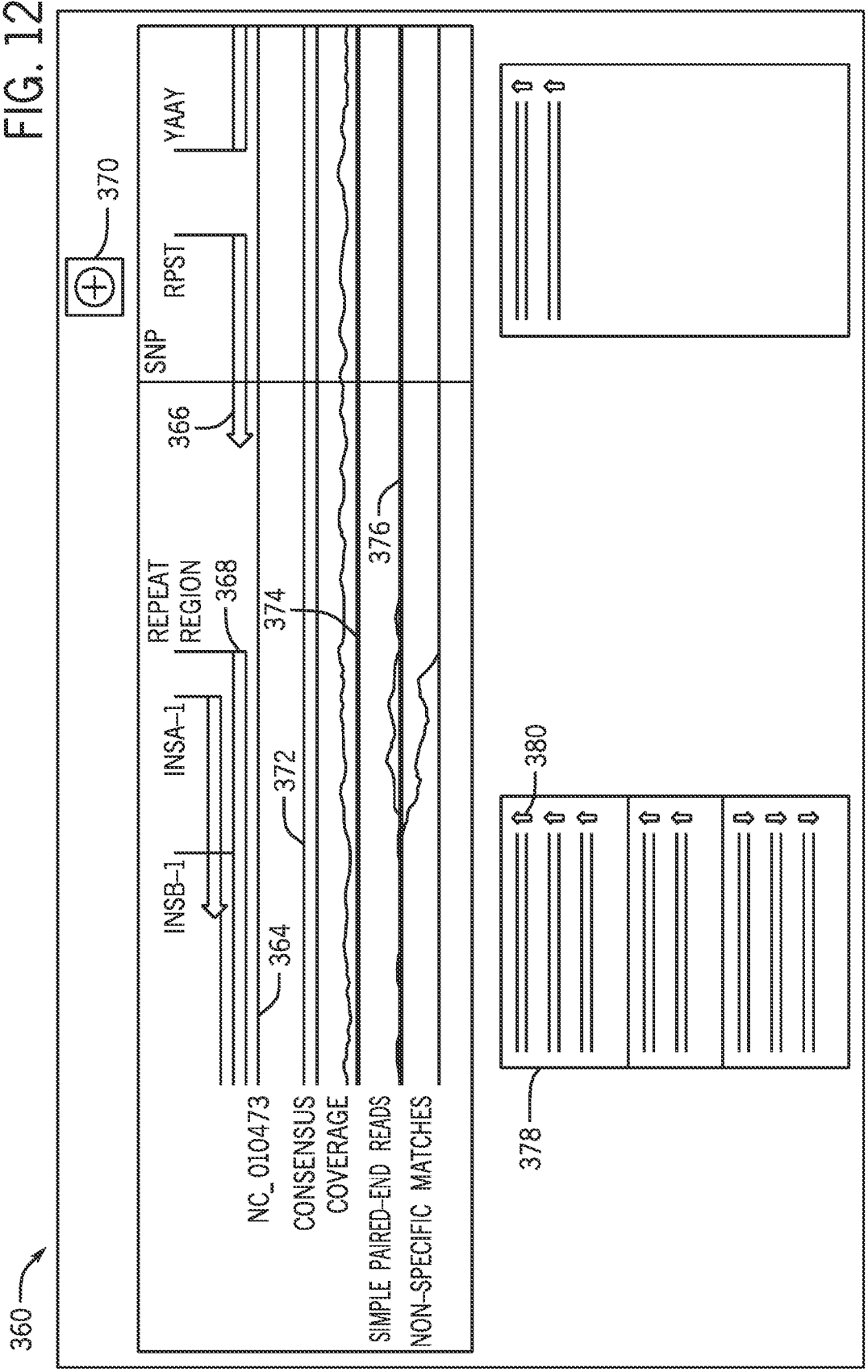
FIG. 12 is an example of display screen showing an annotated portion of sequence data that may be modified by authorized users.

FIG. 12 is an example of a display screen facilitated by the cloud computing environment 12, including an example of sequence data 364 that may be viewed by a group of secondary users. The sequence data 364 may include annotations or marker information 366 and 368. Further, the displayed information may include links or linkable icons 370 for relevant data analysis applications or further information related to the depicted portion of the sequence data. The sequence data 364 may include quality data or other related information 372, 374, and 376 that may facilitate determining if individual nucleotide variants are valid base calls or if particular sequence portions lack sufficient data. In addition, the cloud computing environment 12 may facilitate a commenting or annotating platform associated with the sequence data 364 in which user-contributed annotations 378 may be rated with up or down votes 380 (or other quality markers). Such comments may be useful for determining which contributions are of higher quality. The platform may include a monitoring module for removing annotations of sufficiently low quality and advancing annotations of higher quality to the top. Alternatively, higher quality annotations may be indicated with a color or other graphical identifier (e.g., solid text vs. shadow text for lower quality annotations).

The linkable icons 370 may be linked to relevant apps or applications. Clicking the link may take the user to an application store for data analysis or other tools from third party vendors. Because users will have a wide variety of data sets stored in the cloud, ranging in both size and the nature of their content, different application may be appropriate for different types of data sets. In one embodiment, the applications may be provided as a flat rate or may be charged to the user on a cost-per-run. For example, the application store may be capable of providing feedback to inform a user as to the cost of running a particular application on a particular data set. Such prices are likely to vary widely as different data sets will require widely varying amounts of CPU and storage for processing. The feedback may be based on the size of the stored data set as well as the features of the application in question.

In one embodiment, when the user selects a stored sequence data set and an application to run on that data set, the cloud computing environment 12 executes an algorithm (that may be provided by the application vendor) that uses parameters of the selected user data set (e.g. size) and returns as feedback to the user the price the application vendor will charge to run the application on that data set. After the price is displayed to the user, the user may elect to run, or not run, the application based on whether that price is acceptable. In another embodiment, multiple application vendors may bid on running a common tool, e.g., alignment, via their applications on a particular data set, and the user may choose the most cost effective and/or otherwise desirable run.

In addition to providing a community or shared commenting model for genome annotation, the cloud computing environment 12 may also facilitate genome sharing via a brokerage system. A user may offer a particular genome for viewing via an exchange model (e.g., a trade of access for two or more users, each with respective sequence data available to share) or via a bidding model (e.g., a bid system for access to a particular set of sequence data). The cloud computing environment 12 may also provide a subscription service for access to particular sequence data under the terms of the subscription. Further, clients may indicate a "wish to buy" for sequence data having particular characteristics.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sequencing device, comprising:
   an imager configured to acquire image data from sequencing runs;
   a computer programmed to execute instructions to:
   generate sequence data from the image data;
   communicate device diagnostic information relating to the sequencing device to a cloud computing environment, wherein a manufacturer of the sequencing device is authorized to receive the device diagnostic information and not the sequence data, and wherein the device diagnostic information comprises information about a number of the sequencing runs performed by the sequencing device;
   determine that the sequencing device needs maintenance based at least in part on the device diagnostic information; and
   generate a notification related to the maintenance of the sequencing device.

2. The sequencing device of claim 1, wherein the maintenance comprises a software update.

3. The sequencing device of claim 1, wherein the computer is further programmed to:
   generate the device diagnostic information based on a diagnostic test.

4. The sequencing device of claim 3, wherein the diagnostic test is a check for bugs or errors.

5. The sequencing device of claim 3, wherein the computer is further programmed to communicate results of the device diagnostic check to the cloud computing environment.

6. The sequencing device of claim 1, wherein the device diagnostic information comprises one or more sequencing parameters of the sequencing runs.

7. The sequencing device of claim 1, wherein determining that the sequencing device needs maintenance is based at least in part on a notification received from a cloud computing environment.

8. A method, comprising:
   generating sequence data using a sequencing device performing sequencing runs;
   communicating the sequence data to a cloud computing environment;
   communicating permissions to the cloud computing environment, wherein the permissions authorize access to define a set of authorized users for the sequence data and to diagnostic information, the diagnostic information comprising information about a number of the sequencing runs performed by the sequencing device;
   communicating the diagnostic information of the sequencing device to the cloud computing environment, wherein a manufacturer of the sequencing device is authorized to access an authorized user of the diagnostic data;
   determining that the sequencing device needs maintenance based at least in part on the diagnostic information; and
   generating a notification related to the maintenance of the sequencing device.

9. The method of claim 8, wherein the diagnostic information does not comprise the sequence data.

10. The method of claim 8, comprising discarding the sequence data after communicating the sequence data to the cloud computing environment.

11. The method of claim 8, comprising receiving user instructions comprising the permissions.

12. A sequencing device, comprising:
    an imager configured to acquire image data from sequencing runs;
    a computer programmed to execute instructions to:
    generate sequence data from the image data;

communicate device diagnostic information relating to the sequencing device to a cloud computing environment, wherein a manufacturer of the sequencing device is authorized to receive the device diagnostic information and not the sequence data, and wherein the device diagnostic information comprises information about a number of the sequencing runs performed by the sequencing device; and receive a notification from the cloud computing environment that the device needs maintenance, wherein the notification is based on the device diagnostic information.

13. The sequencing device of claim 12, wherein the maintenance comprises a software update.

14. The sequencing device of claim 12, wherein the computer is further programmed to communicate the sequence data or a notification to access the sequence data based on a set of permissions.

15. The sequencing device of claim 12, wherein the sequence data is from an individual sequencing run of the sequencing runs.

\* \* \* \* \*